United States Patent [19]

Morris

[11] Patent Number: 5,161,544
[45] Date of Patent: Nov. 10, 1992

[54] SURGICAL DRAPE HAVING 360 DEGREE FLUID CONTROL

[75] Inventor: H. Krzewinski Morris, Arlington, Tex.

[73] Assignee: Johnson & Johnson Medical, Inc., Arlington, Tex.

[21] Appl. No.: 493,567

[22] Filed: Mar. 14, 1990

[51] Int. Cl.⁵ .................... A61B 19/00; A61B 19/08
[52] U.S. Cl. ................................... 128/849; 128/853
[58] Field of Search ............................ 128/849–856

[56] References Cited

U.S. PATENT DOCUMENTS

| | | | |
|---|---|---|---|
| 3,650,267 | 3/1972 | Anderson | 128/132 |
| 3,667,458 | 6/1972 | Krebs | 128/853 |
| 3,923,052 | 12/1975 | Zoephel | 128/853 |
| 4,007,741 | 2/1977 | Waldrop | 128/292 |
| 4,036,235 | 7/1977 | Hathaway | 128/292 |
| 4,105,019 | 8/1978 | Haswell | 128/132 |
| 4,201,212 | 5/1980 | Bradley | 128/275 |
| 4,378,794 | 4/1983 | Collins | 128/853 |
| 4,414,968 | 11/1983 | Amin | 128/132 |
| 4,462,396 | 7/1984 | Wichman | 128/132 |
| 4,559,937 | 12/1985 | Vimson | 128/132 |
| 4,570,628 | 2/1986 | Neal | 128/853 |
| 4,596,245 | 6/1986 | Morris | 128/853 |
| 4,598,458 | 7/1986 | McAllester | 128/132 |
| 4,616,642 | 10/1986 | Martin | 128/853 |
| 4,730,609 | 3/1988 | McConnell | 128/853 |
| 4,869,271 | 9/1989 | Idris | 128/853 |
| 4,890,628 | 1/1990 | Jackson | 128/849 |

Primary Examiner—Michael A. Brown

[57] ABSTRACT

Devices for collecting fluids from a patient are disclosed. The present invention includes a first sheet of liquid impervious material having an opening. The first sheet is attached to a bottom sheet of liquid impervious material having a fenestration for access to the patient. A bendable section disposed along the inner perimetric edge of the first sheet retain the edge in a particular defined shape, improving fluid collection and access. The bendable section preferably includes a wire covered by a pliable plastic material, which are encased by providing a second sheet of liquid impervious material and placing the bendable section between the first second sheets. The sheets are then preferably secured by heat sealing. In certain preferred embodiments adhesive is provided on the patient facing side of the fenestration section and drainage ports for transmitting fluids are affixed to the bottom sheet. The present invention also provides a surgical drape including a sheet of drape material having an opening for access to the patient and having a device for collecting fluids as described above attached to it. Such drapes may also include a pad of absorbent material overlying the drape material and a device for retaining a drainage tube. Methods of manufacturing a fluid collecting device are also disclosed.

30 Claims, 5 Drawing Sheets

SURGICAL DRAPE HAVING 360 DEGREE FLUID CONTROL

The present invention relates to devices for collecting fluid from a patient and more particularly to surgical drapes having means for collecting and controlling the fluids which accumulate during surgical procedures, such as Caesarian section deliveries.

BACKGROUND OF THE INVENTION

During most surgical procedures blood and other body fluids are released. Additionally, most procedures require some irrigation, resulting in additional fluid in the area of the incision. Many times it is impractical to collect and control this fluid using suction, and therefore the fluid is permitted to seep into the area surrounding the incision or location where the procedure produces a fluid flow. Surgical drapes comprising a sheet of flexible material having a fenestration and a spaced apart region for collecting the fluids and materials emanating from the patient during the surgical procedure are well known. For example, U.S. Pat. No. 4,462,396—Wichman discloses a drape having a flexible pocket secured to top surface of a drape. A fitting attached to the pocket permits a tube to be utilized to drain the pocket of the fluids collected. Similarly, U.S. Pat. No. 4,559,937—Vinson and U.S. Pat. No. 4,598.458—McAllester disclose surgical drapes having fluid collection bags spaced at a location whereby the fluid will flow by gravity and be collected and stored.

Although fluid collection and control is important in most surgical procedures, many gynecological and obstetric procedures pose particularly difficult problems. In the past, others have attempted to provide fluid collection means particularly adapted to collecting these such fluid flows. A surgical drape for cystoscopic procedures having a fenestration and a folded pocket located in the path of the fluid runoff is disclosed in U.S. Pat. No. 4,414,968—Amin. Although using apparatus separate from the surgical drape itself, a method of collecting postpartum fluid is disclosed in U.S. Pat. No. 4,105,019—Haswell. The method disclosed utilizes a sheet-like receptacle having two pockets one for collecting amniotic fluid and one for collecting blood. A fluid collection apron for use during transurethral resection is disclosed in U.S. Pat. No. 4,007,741—Waldrop, et al. The apron is attached to the urological operating table and to the surgeon's neck. The apron collects fluid and drains it through a tube into a remote collection receptacle.

In addition to the specific examples discussed above, it is also well known within the art to design surgical drapes and the like to be particularly adapted to operations performed on certain body portions, and indeed, adapted to specific procedures. For example, in the case of the ear, specific drainage devices for collecting fluid and channeling the fluid to a remote receptacle have been disclosed in U.S. Pat. No. 4,036,235—Hathaway and U.S. Pat. No. 4,201,212—Bradley. Both designs rely upon the patient being in an upright position, providing a fenestration disposed above a fluid collection pouch, thereby providing a gravity flow generally the patient into the collection pouch.

One disadvantage to the methods and apparatus disclosed immediately above is that the fluid collection pouch is spaced or disposed on the patient in a manner which relies on patient orientation to provide a gravity flow in a particular direction. Thus, if the patient were to shift or if the surgeon required the patient to be reoriented, it would also be necessary to re-orient the drape and fluid collection apparatus to some extent. A solution to this problem is provided by U.S. Pat. No. 3,650,267—Anderson, which discloses a surgical drape having a fluid collection means surrounding the area adjacent to the fenestration. The apparatus disclosed consists of a very thin flexible bag having a fenestration formed in its bottom and preferably having a rim of elastic or other material sewn to the upper portion which forms an open end. In certain embodiments a tubular drain is integrated into the fluid collector. On problem with such a device, however, is that the edges of the bag tend to become matted down during the procedure, resulting in fluid spillage.

It therefore would be desireable to provide a fluid collection device which could be readily integrated into a variety of drapes and adapted to a variety of procedures. Such a drape would preferably collect fluids and other materials from the entire periphery of an incision wound or fluid source and would not rely substantially upon the exact orientation of the patient.

SUMMARY OF THE INVENTION

Accordingly, it has now been found that a device for collecting fluids from a patient which overcomes the problems associated with previous designs, while improving the efficiency of fluid collection and providing an enhanced surgical site can be constructed. The apparatus disclosed by the present invention provides one or more bendable means disposed substantially along the inner perimetric edge of a thin pliable sheet of liquid impervious material. The device comprises a first sheet of liquid impervious material having an opening. The first sheet is attached to a bottom sheet of liquid impervious material having a fenestration for access to the patient. The bendable means retain the inner perimetric edge of an opening in the top sheet in a defined shape improving fluid collection and access. The bendable means are preferably formed of a metallic section embedded in a cover, such as a wire covered by a pliable plastic material.

Preferably, the bendable means are encased by providing a second sheet of liquid impervious material and placing the bendable means between the first second sheets. The second sheet may be in registration with the first sheet and secured in a liquid tight relationship at least along the inner and outer perimetric edges. Alternatively, the second sheet may be comprised of an annular section of material, secured in a liquid tight relationship to the first sheet along the inner perimetric edge. Preferably, the sheets are secured by heat sealing. In certain embodiments the fenestration section is secured to the bottom sheet in a liquid tight relationship, preferably by heat sealing.

In a preferred embodiment, a portion of said bottom sheet is coated with adhesive on said patient facing side and most preferably, the fenestration section is coated with adhesive. Certain embodiments also comprise drainage ports for transmitting fluids which are affixed to the bottom side.

The present invention also provides a surgical drape for overlying a patient comprising a sheet of drape material having at least one opening for access to the patient and having a device for collecting fluids as described above attached thereto. Drapes disclosed also comprise a pad of absorbent material overlying said drape material and means for retaining a drainage tube. Methods of manufacturing a fluid collecting device are also disclosed.

DETAILED DESCRIPTION OF THE PREFERRED EMBODIMENTS

Figures 1, 2, 2A:
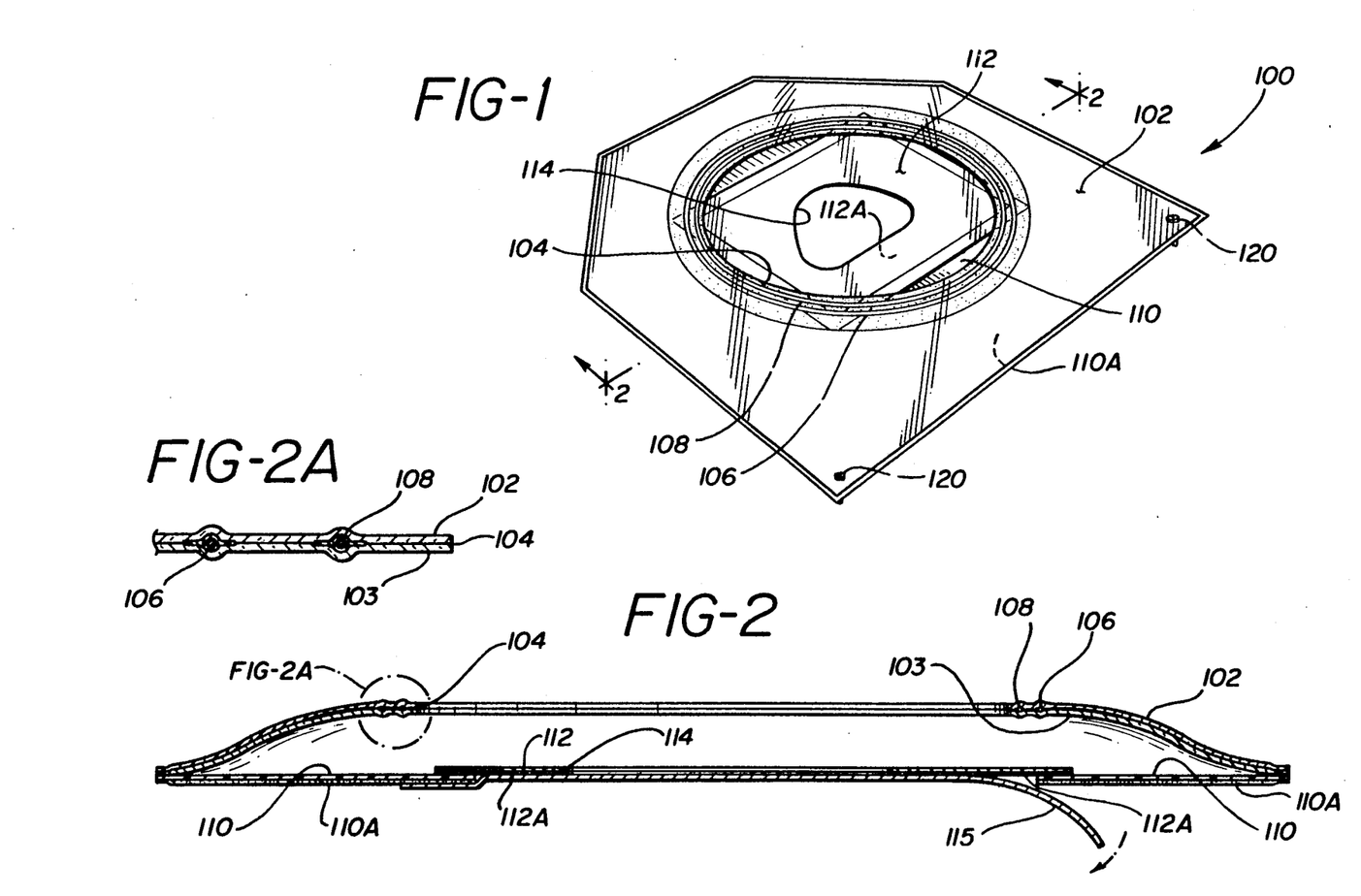
FIG. 1 is an isometric view of a fluid control apparatus made in accordance with the present invention.
FIG. 2 is a cross-section of the fluid control apparatus of FIG. 1, taken along line 2—2.
FIG. 2A is an enlarged view of a portion of the fluid control apparatus shown in FIG. 2.

Referring to FIG. 1 an isometric view of fluid control apparatus 100 made in accordance with the present invention is shown. The fluid control apparatus is comprised of a top sheet 102, which is preferably thin pliable sheet of fluid impervious material, which is most preferably substantially transparent. The top sheet 102 has an opening, thus creating both an outer perimetric edge and an interior perimetric edge 104, the latter defining the opening. Affixed to the top sheet 102 near the interior perimetric edge is at least one elongated, flexible, bendable support element 106 adjacent to and substantially completely surrounding the interior perimetric edge. The thin bendable element 106 is preferably comprised of a plastic encased wire, similar to the construction of a twist tie typically used as a closure device for various types of bags. As shown in FIG. 1, in a preferred embodiment, a second thin bendable element 108 is also provided.

The bendable elements 106, 108 are preferably placed in contact with one of the surfaces of the top sheet 102 and are held in place by a number of techniques, for example, they may be affixed using adhesives, or by heat sealing the bendable elements 106, 108 to the top sheet or to the top sheet 102 and a second sheet 103 of similar material. The bendable elements 106, 108 are constructed from a wire having a sufficiently heavy gauge to maintain the edge of the opening in the top sheet in place and in a configuration which promotes fluid collection. By manipulating the bendable elements, it is possible to form the edge of the top sheet into an upwardly depending lip and the bendable means will retain it in such a position, preventing fluid from flowing over this edge on to the top sheet 102. The present invention thus keeps the fluid contained within the top and bottom sheets, which are sealed together in a liquid tight relationship to form container, i.e., a pouch. However, unlike a more rigid structure, the bendable elements do not substantially inhibit the characteristics of the surrounding thin pliable sheets 102, 110 and further provide a structure which adds very little bulk when the device is folded and packaged.

The bendable elements 106, 108 of the present invention create a relatively more rigid and shape retentive section along the inner perimetric edge 104 of this section of the fluid collection device. Numerous materials and constructions can be substituted to achieve a similar effect. For example, certain shape retentive foam materials could be formed in thin strips or narrow annular sections and disposed in the manner of the bendable elements 106, 108 shown. It is preferred, however, that a plastic encased wire as described be used.

As will be explained in further detail below, the fluid control apparatus of the present invention also comprises a bottom sheet 110, preferably is also comprised of a thin pliable sheet of material. The bottom sheet 110 also has a fenestration section 112 which is placed into contact with the patient. The fenestration section has an interior perimetric edge 114 which defines the fenestration through which the surgeon may access the patient during a procedure. Preferably, the side of the fenestration section which contacts the patient is coated with an adhesive material 112A. In certain embodiments, either the fenestration section or the entire patient facing bottom sheet may be coated with an anti-microbial coating 110A. This coating may be in addition to an adhesive or may be used alone, for example, only the fenestration section might be coated with adhesive, while the fenestration section 112 and the rest of the bottom sheet, i.e., the entire bottom sheet 110 may be coated with an anti-microbial product. One such coating is Micro-Side TM which is comprised of polyhexamethylenebiguanide (PHMB). Also, one or more drainage ports 120 are provided in the bottom sheet 110 in order to facilitate the removal of the collected fluid from the fluid collection device 110 illustrated. In ceratin embodiments, the fenestration section 112 may be integral with the bottom sheet 110.

Further details of the construction of the fluid collection device depicted in FIG. 1 are seen in the cross-sectional view of FIG. 2. As shown, the top sheet 102 also preferably comprises a second sheet of thin pliable material 103. In a preferred embodiment, the top sheet 102 and second sheet 103 are thermally bonded in the region of the interior perimetric edge to retain the bendable elements 106, 108 in place and also at the outer edge of the device thereby creating a liquid tight seal between the top sheet 102, the second sheet 103 and the bottom sheet 110. The construction of the region near the interior edge 104 of the top sheet is shown in the enlarged view of FIG. 2A. The bendable means 106, 108 are spaced apart from each other and the edge 104 of the opening, and are sealed between the top sheet 102 and second sheet 103. In certain embodiments, it may be preferable to use a single bendable means or to replace the encased wire depicted with other shapes or materials. The design of the bendable means will depend largely upon the material characteristics and thickness of the top sheet 102 and second sheet 103, as well as the overall size of the fluid collection device 100 and the opening.

Referring again to FIG. 2, the construction of the lower section of the fluid collection device of the present invention is shown. The bottom sheet 110 preferably surrounds an adhesive fenestration section 112. The bottom sheet 110 and fenestration section 112 are preferably heat sealed or otherwise affixed to provide a liquid tight seal at their juncture. In a preferred embodiment, the bottom sheet 110 is comprised of a substantially opaque portion, while the fenestration section 112 and the adhesive disposed thereon are substantially transparent. A protective covering, such as release paper 115 overlies the adhesive on the fenestration section 112 and is removed prior to use, as shown by the arrow in FIG. 2.

Figure 3:
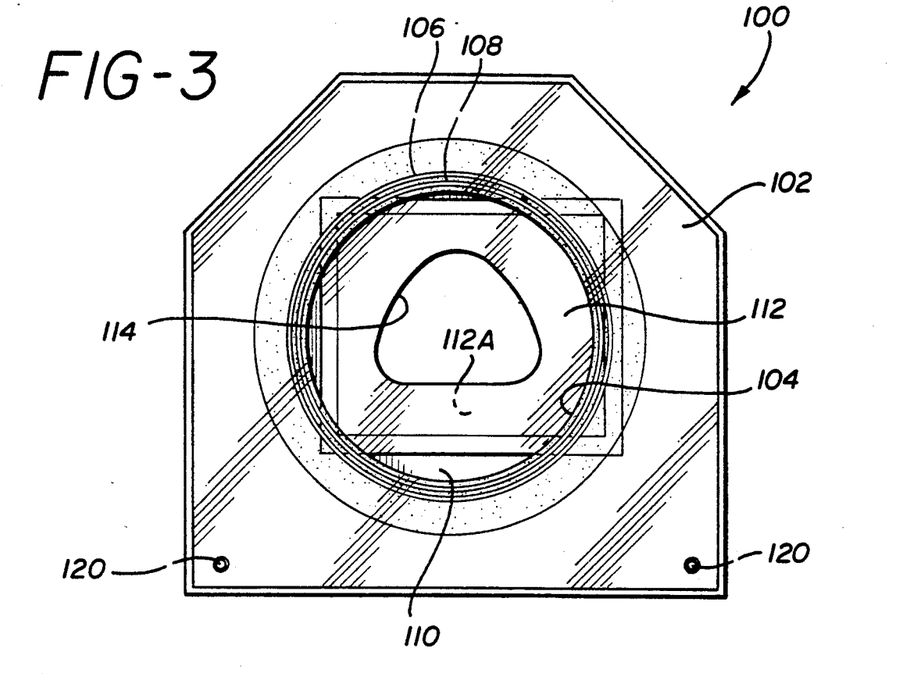
FIG. 3 is a top plan view of the apparatus shown in FIG. 1.

A top plan view of a preferred embodiment of the fluid collection device 100 of the present invention is depicted in FIG. 3. The device 100 shown is particularly adapted for use in a procedure such as a Caesarean section delivery, during which a relatively large quantity of fluids and other materials are released and must be channeled away from the incision and collected. Accordingly, the present invention provides the capability to collect fluids around the entire perimeter of the incision—that is, 360 degree collection. The device 100 is most preferably in the substantially square or rectangular, having two corners removed at about a 45 degree angle, resulting in the shape shown. Numerous other overall shapes will be useful, however, depending upon the application for a particular surgical procedure. In use, the fenestration section 112 will be placed into substantially fluid tight contact with the portion of the patient surrounding the incision site. Fluids will flow from all directions on to the top surface of the fluid impervious sheet which comprises the fenestration section 112 and the bottom sheet 110. Most preferably, the drainage ports 120 are located to take best advantage of gravity when the fluid collection apparatus is placed on the patient. In the case of the preferred embodiment shown, the drainage ports 120 are located in the corners of one side of the device, where the fluids and materials will collect and be drained. Although visible in this view because the top sheet 102 is preferably transparent, the drainage ports 120 are disposed on the bottom sheet 110. Also, in the preferred embodiment shown, the fenestration section 112 is slightly offset from the opening in the top sheet. This design is preferred since the incision made for a Caesarean section is typically offset from the central medial plane of the patient, therefore the fenestration is disposed at an offset position while the collection device itself remains substantially atop the patient.

Figure 4:
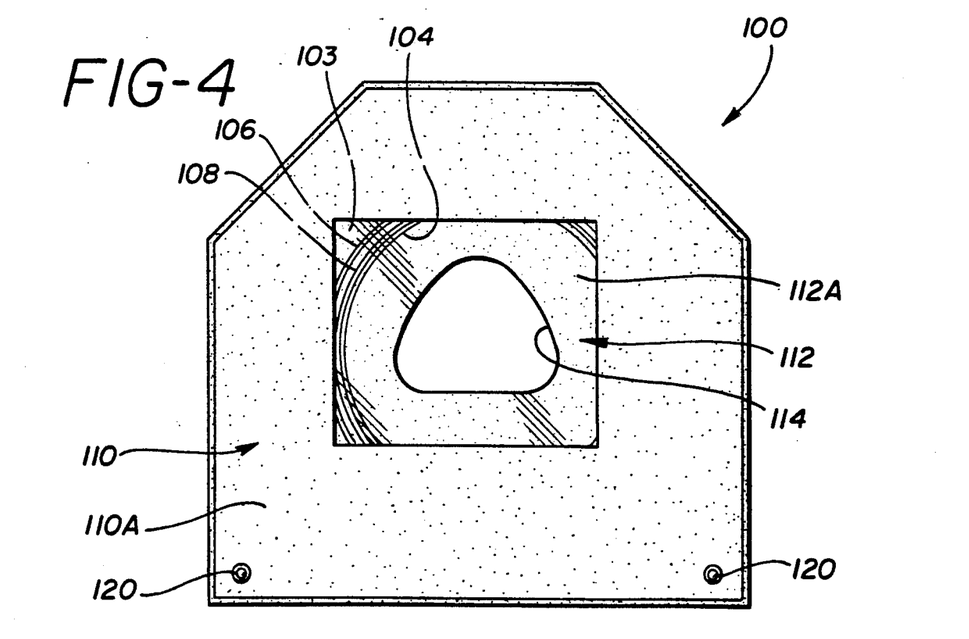
FIG. 4 is a bottom plan view of the apparatus shown in FIG. 1.

Referring to FIG. 4, a bottom plan view of a preferred embodiment of a fluid collection device 100 made in accordance with the present invention is shown. As set forth above, the drainage ports 120 which are located on the bottom sheet 110 are seen in this view. The fenestration section 112, upon which adhesive is preferably applied is also shown. Since the fenestration section 112 is preferably transparent, the second sheet 103 and the top sheet 102, as well as the bendable elements 106, 108 are all visible in FIG. 4.

Figure 5:
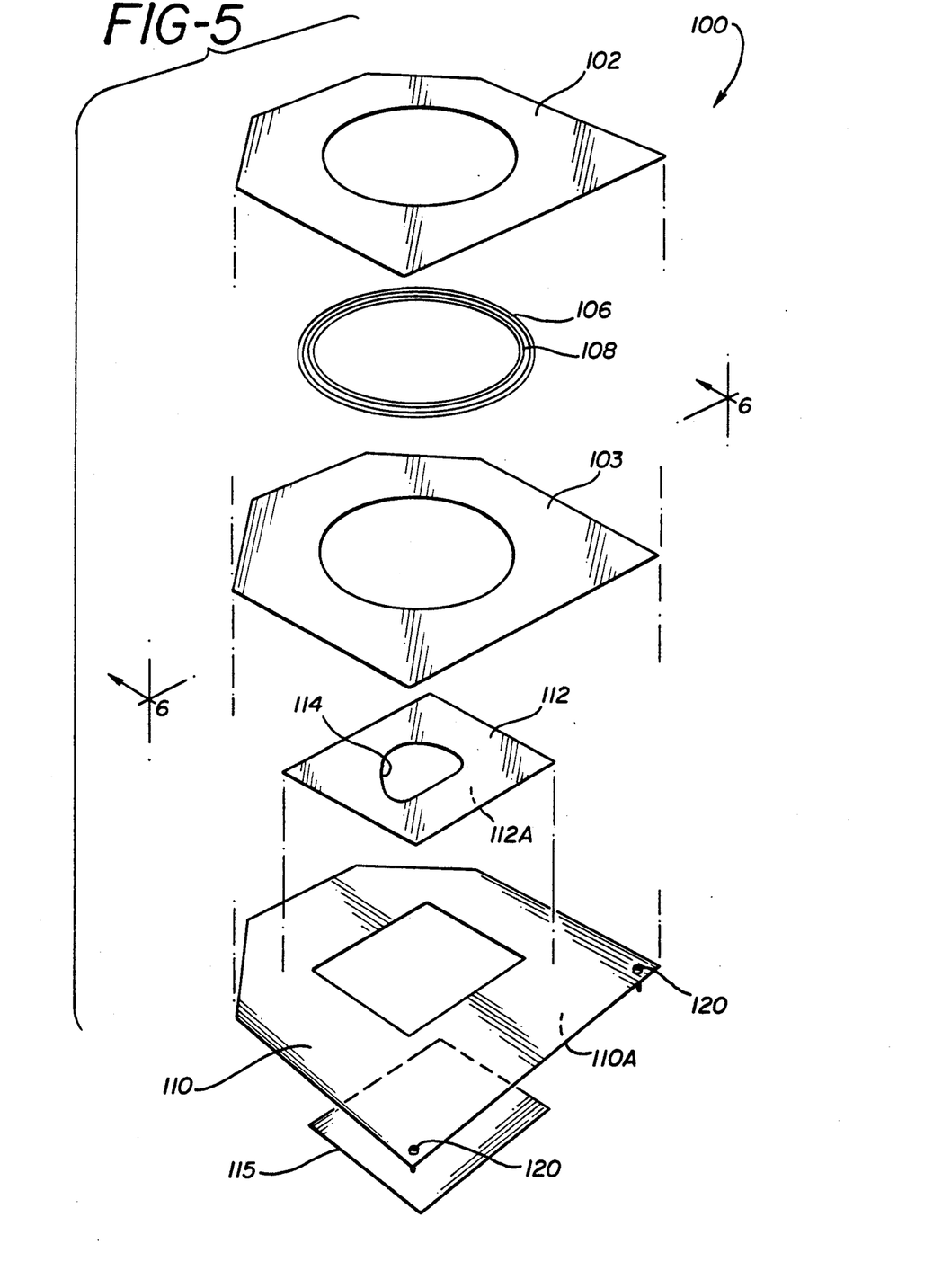
FIG. 5 is an exploded isometric view of the fluid control apparatus shown in FIG. 1.

The placement of the components which form the preferred embodiment of the fluid collection device made in accordance with the present invention are shown in the exploded isometric view of FIG. 5. Preferably, bendable means 106, 108 are disposed between the top sheet 102 and second sheet 103, which are then preferably bonded together by heat sealing or applying adhesives in at least the region of the bendable means 106, 108, thereby embedding them in place. The bottom section is formed by affixing the fenestration section 112 to one side of the bottom sheet 110, again preferably by heat sealing or applying an adhesive. The side of the fenestration section 112 placed into contact with the bottom sheet 110 is the side which preferably has adhesive disposed thereon. Accordingly, release paper 115 is placed over the adhesive and removed prior to use. The drainage ports 120 are also installed on the bottom sheet 110. The upper and lower sections are then joined and a liquid impervious seal is formed about the outer perimetric edges of the top sheet 102, the second sheet 103 and the bottom sheet 110, resulting in a complete fluid collection device, substantially as depicted in FIG. 1.

Figure 6:
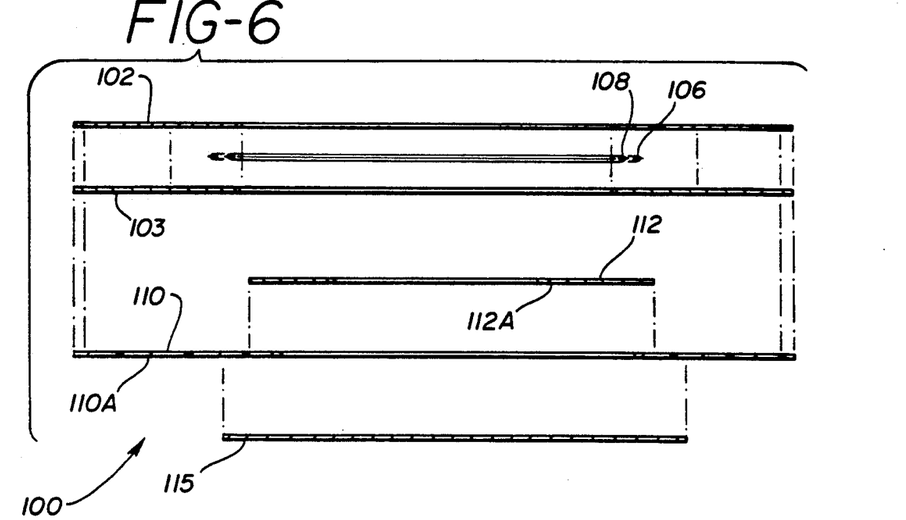
FIG. 6 is a side view of the exploded fluid control apparatus construction depicted in FIG. 5.

A side view of the construction described in FIG. 5, taken along line 6—6, is shown in FIG. 6. As shown by the single connecting lines, the fist sheet 102, second sheet 103 and bendable means 106, 108 are disposed atop one another and form an upper section of the device. The bottom sheet 110, fenestration section 112 and cover paper 115 form a lower section. As indicated by the double connecting lines, the upper section and lower section are preferably then joined and sealed around their outer perimetric edges to form a complete fluid collection device 100.

Although the fluid collection device 100 described above with reference to FIGS. 1–6 may be used alone as a fluid control product, it is also a preferred embodiment of the present invention to incorporate the fluid collection device 100 into a drape or other structure which covers the patient. As shown in isometric view in FIG. 7, an obstetric drape 200 for use during procedures such as a Caesarean sections is provided by the present invention. A fluid collection device 100 is disposed upon and attached to the surface of a drape 210. As well known to those of ordinary skill, numerous materials can be utilized as surgical drapes including woven and nonwoven fabrics and polymeric materials. In a preferred embodiment an instrument pad 220 is also disposed upon the top surface of the drape 210. The instrument pad provides a reinforced section and preferably absorbent surface upon which instruments or other objects may rest during the procedure. The instrument pad 220 is also provided with one or more means for retaining a drainage tube 222. Preferably, while in use, a tube will connect the drainage ports 120 with a remote collection receptacle (not shown). The retaining means 222 are provided to keep the tube in proper position and away from the area of the incision.

Figure 7:
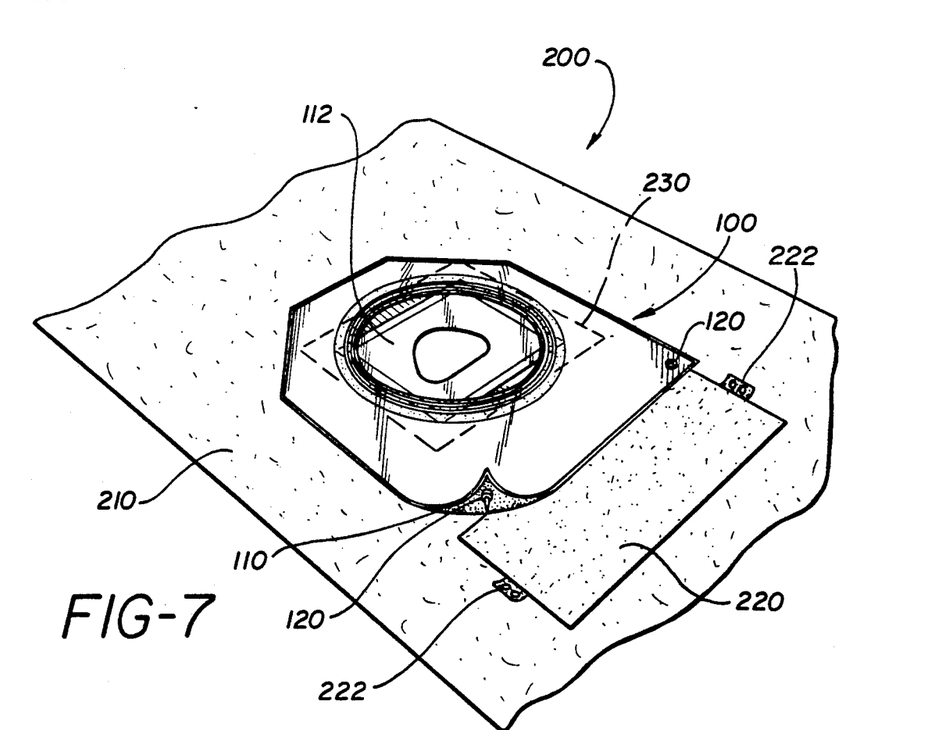
FIG. 7 is an isometric view of the fluid control apparatus portion of FIG. 1, shown installed on a portion of a surgical drape.

The fluid collection device 100 is preferably affixed to the drape 210 substantially along the along the dashed line 230 shown in FIG. 7. By affixing the fluid collection device 100 to the drape surface 210 in this manner, the characteristics of the drape material are not affected by the fluid collection device. In other words, the drape material retains the same degree of conformability to the patient, except in a small area near the fenestration section 112. As easily envisioned by those of ordinary skill, such a construction is advantageous, particularly as the fluid collection device becomes filled with fluid, since it may move relative to the drape material 210 and, thus will not substantially shift or otherwise affect the position of the drape. As seen by the upturned corner illustrated in FIG. 7, The drainage port protrudes from the bottom sheet 110 and is preferably located over the instrument pad 220 when in use.

Figure 8:
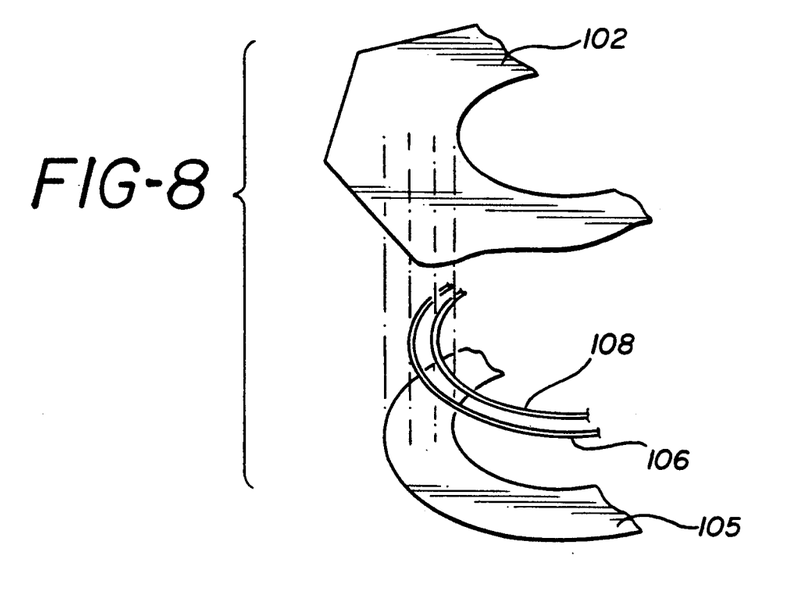
FIG. 8 is a partially broken away exploded isometric view, similar to FIG. 5, of an alternative construction of a portion of the present invention.

As an alternative to the construction disclosed above with reference to FIGS. 1–6, the top section may be formed as shown in FIG. 8. As shown in a partial exploded isometric view, similar to FIG. 5, the bendable means 106, 108 may be contained between the top sheet 102 and an annular layer 105, which replaces the second sheet 103 described above. In this embodiment, the top section will therefore comprise two layers only in the region surrounding the interior perimetric edge where the bendable means 106, 108 are disposed. The desirability of this type of construction is again determined by the thickness and other characteristics of the materials used, and the particular application for the drape being designed.

Figure 9:
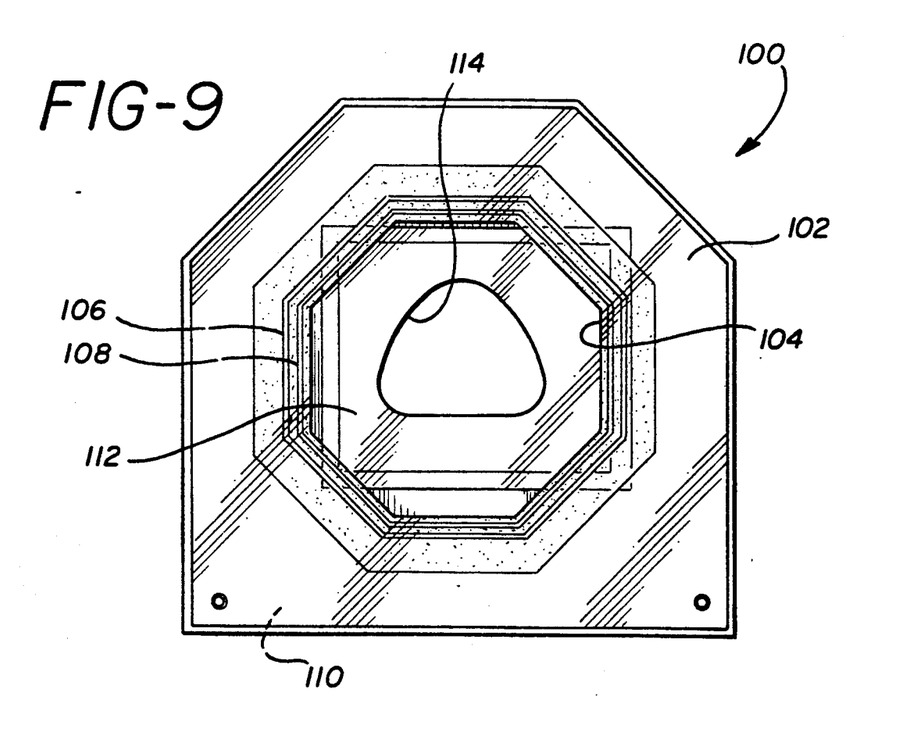
FIG. 9 is a top plan view, similar to FIG. 3 of an alternative design of the present invention.

Referring to FIG. 9 and alternate design of the fluid collection device 100 of the present invention is shown in a top plan view, similar to that of FIG. 3. In this embodiment, the interior perimetric edge 104 of the top sheet 102 and second sheet 103 (or annular section 105), as well as the bendable means 106, 108 are substantially octagonally shaped. In certain applications, this design might be preferred because the sides of the opening in the top section are substantially parallel to five of the sides of the outer perimetric edge of the device. Therefore, improved draping characteristics and improved stability and uniformity in the performance of the bendable means to keep the opening properly positioned above the bottom sheet 110 and fenestration section 112 are obtained.

Numerous variations to the invention disclosed above will present themselves to those of ordinary skill. Accordingly, reference should be made to the appended claims in order to determine the scope of the present invention.

What is claimed is:

1. A device for collecting fluids from a patient comprising:
   a bottom sheet of liquid impervious material comprising a fenestration for access to the patient, having a patient facing side and outwardly facing side;
   a first sheet of liquid impervious material having an outer perimetric edge and an opening defined by an inner perimetric edge, said first sheet being secured to said outwardly facing side of said bottom sheet in liquid tight relationship along a line that completely surrounds said fenestration; and
   one or more bendable means disposed substantially along said inner perimetric edge, whereby said bendable means retain said inner perimetric edge in a defined shape above said bottom sheet.

2. The device of claim 1, further comprising a second sheet of liquid impervious material and wherein said bendable means are disposed between said first sheet and said second sheet.

3. The device of claim 2, wherein said second sheet is substantially in registration with said first sheet and said first and second sheets are secured to each other in a liquid tight relationship at least along said inner perimetric edge and said outer perimetric edge.

4. The device of claim 3, wherein said first and said second sheets are secured by heat sealing.

5. The device of claim 3, wherein said first and said second sheets are secured by adhesive means.

6. The device of claim 2, wherein said second sheet is comprised of an annular section of material, secured in a liquid tight relationship to said first sheet substantially along said inner perimetric edge.

7. The device of claim 6, wherein said first and said second sheets are secured by heat sealing.

8. The device of claim 6, wherein said first and said second sheets are secured by adhesive means.

9. The device of claim 1, wherein said bottom sheet comprises a fenestration section having said fenestration therein and secured to said bottom sheet in a liquid tight relationship.

10. The device of claim 9, wherein said bottom sheet and said fenestration section are secured by heat sealing.

11. The device of claim 9, wherein said bottom sheet and said fenestration section are secured by adhesive means.

12. The device of claim 9, wherein said fenestration section is coated with adhesive on said portion of said bottom sheet.

13. The device of claim 12, further comprising an anti-microbial coating applied to said fenestration section.

14. The device of claim 1, wherein at least a portion of said bottom sheet is coated with adhesive on said patient facing side.

15. The device of claim 14, further comprising an anti-microbial coating applied on said patient facing side.

16. The device of claim 1, further comprising at least one drainage port means for transmitting fluid affixed to said bottom side.

17. The device of claim 1, wherein said opening defined by an inner perimetric edge is substantially circular.

18. The device of claim 1, wherein said opening defined by an inner perimetric edge is substantially octagonal.

19. The device of claim 1, wherein said bendable means comprise a metallic section embedded in a cover.

20. The device of claim 19, wherein said metallic section comprises a substantially cylindrical wire means and said cover comprises a pliable plastic material.

21. A surgical drape for overlying a patient comprising:
   a sheet of drape material having at least one opening therein for access to the patient;
   a device for collecting fluids from the patient, attached to said drape material and overlying said opening, said device comprising a bottom sheet of liquid impervious material comprising a fenestration for access to the patient, having a patient facing side and outwardly facing side;
   a first sheet of liquid impervious material having an outer perimetric edge and a further opening defined by an inner perimetric edge, said first sheet being secured to said outwardly facing side of said bottom sheet in liquid tight relationship along a line that completely surrounds said fenestration;
   one or more bendable means disposed substantially along said inner perimetric edge, whereby said bendable means retain said inner perimetric edge in a defined shape above said bottom sheet.

22. The surgical drape of claim 21, further comprising a pad of absorbent material overlying said drape material.

23. The surgical drape of claim 22, further comprising means for retaining a drainage tube.

24. A disposable surgical drape comprising:
   a first thin pliable sheet of liquid impervious material having an outer perimetric edge and an opening defined by an interiorly located perimetric edge of said first sheet;
   a bottom sheet comprised of a thin pliable sheet of liquid impervious material having an outer perimetric edge and a fenestration defined by an interiorly located perimetric edge of said bottom sheet;
   said first and said bottom sheets being secured to each other in liquid tight relationship inwardly of the outer perimetric edge of at least one of said first and said bottom sheets;

at least one elongated, flexible, bendable support element adjacent to and substantially completely surrounding said opening and in contact with one or said surfaces of said first sheet for retaining said inner perimetric edge of said first sheet above said bottom sheet;

a second thin pliable sheet of liquid impervious material secured to one surface of said first sheet in the region adjacent said opening, said at least one bendable element being located between said first and second sheets.

25. The drape of claim 24, wherein said first and second sheets are secured to said at least one bendable element so as to prevent movement of said element with respect to said first and second sheets.

26. The drape of claim 24, wherein said first and second sheets are secured to each other at least in the region of said bendable element.

27. A method of manufacturing a fluid collecting device comprising the steps of:

providing a first and second sheet of thin pliable liquid impervious material having an opening defined by an inner perimetric edge and at least one bendable means;

forming an upper section by securing said bendable means between said first and second sheets to create a liquid tight seal;

providing a bottom sheet and a fenestration-containing section comprised of thin pliable liquid impervious material;

forming a lower section by securing said bottom sheet and said fenestration-containing section to create a liquid tight seal;

securing said upper section and said lower section together to form a liquid tight seal along a line that completely surrounds said fenestration and to permit said bendable means to retain said inner perimetric edge above said lower section.

28. The method of claim 27, further comprising the steps of applying adhesive to at least a side of said fenestration containing section; and overlying said adhesive with a protective cover.

29. The method of claim 27, wherein at least one of said securing steps comprises heat sealing.

30. The method of claim 27, wherein at least one of said securing steps comprises applying adhesive means.

* * * * *